United States Patent
Gindele et al.

(10) Patent No.: US 10,475,215 B2
(45) Date of Patent: Nov. 12, 2019

(54) CBCT IMAGE PROCESSING METHOD

(71) Applicant: CARESTREAM HEALTH, INC., Rochester, NY (US)

(72) Inventors: Edward B. Gindele, Rochester, NY (US); Richard A. Simon, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 185 days.

(21) Appl. No.: 15/662,670

(22) Filed: Jul. 28, 2017

(65) Prior Publication Data

US 2018/0089864 A1 Mar. 29, 2018

Related U.S. Application Data

(60) Provisional application No. 62/398,585, filed on Sep. 23, 2016.

(51) Int. Cl.
*G06T 11/00* (2006.01)
*A61B 6/00* (2006.01)
(Continued)

(52) U.S. Cl.
CPC ........... *G06T 11/005* (2013.01); *A61B 6/03* (2013.01); *A61B 6/4085* (2013.01); *A61B 6/487* (2013.01); *A61B 6/5205* (2013.01); *A61B 6/5258* (2013.01); *A61B 6/583* (2013.01); *G06T 5/002* (2013.01); *G06T 5/50* (2013.01);
(Continued)

(58) Field of Classification Search
CPC ......... A61B 6/03; A61B 6/4085; A61B 6/487; A61B 6/5205; A61B 6/5258; A61B 6/583; G06T 11/005; G06T 11/008; G06T 5/002; G06T 5/50; G06T 2207/10076; G06T 2207/10081; G06T 2207/20012; G06T 2207/20016; G06T 2211/432
See application file for complete search history.

(56) References Cited

U.S. PATENT DOCUMENTS 5,270,926 A 12/1993 Tam
5,526,446 A * 6/1996 Adelson .................. G06K 9/40
382/260

(Continued)

OTHER PUBLICATIONS

Michal Aharon et al., "K-SVD: An Algorithm for Designing Overcomplete Dictionaries for Sparse Representation," IEEE Transactions on Signal Processing, vol. 54, No. 11, Nov. 2006, pp. 4311-4322.

*Primary Examiner* — Mekonen T Bekele

(57) ABSTRACT

A method for multi-dimensional image processing obtains a multi-dimensional image having a plurality of data elements, each data element having a corresponding data value. The method forms a reduced noise image by repeated iterations of a process that adjusts the data value for one or more data elements p of the obtained image by: for each data element k in a group of data elements in the image, calculating a weighting factor for the data element k as a function of the difference between an estimated data value for data element p and the corresponding data value of data element k, updating the estimated data value for the data element p according to the combined calculated weighting factors and the data value of the data element k; and displaying, storing, or transmitting the reduced noise image.

15 Claims, 6 Drawing Sheets

(51) Int. Cl.
  *G06T 5/50* (2006.01)
  *A61B 6/03* (2006.01)
  *G06T 5/00* (2006.01)

(52) U.S. Cl.
  CPC .. *G06T 11/008* (2013.01); *G06T 2207/10076* (2013.01); *G06T 2207/10081* (2013.01); *G06T 2207/20012* (2013.01); *G06T 2207/20016* (2013.01); *G06T 2211/432* (2013.01)

(56) References Cited

U.S. PATENT DOCUMENTS

| | | | | |
|---|---|---|---|---|
| 5,729,631 A * | 3/1998 | Wober | | G06F 17/147 348/E9.01 |
| 5,999,587 A * | 12/1999 | Ning | | A61B 6/4447 378/4 |
| 6,937,772 B2 | 8/2005 | Gindele | | |
| 7,570,831 B2 * | 8/2009 | Shaked | | G06T 7/40 348/607 |
| 7,840,088 B2 * | 11/2010 | Huang | | G06T 5/002 382/167 |
| 7,889,942 B2 * | 2/2011 | Vakrat | | G06T 5/009 382/254 |
| 8,369,640 B2 * | 2/2013 | Ishiga | | G06T 5/50 358/3.26 |
| 8,385,677 B2 * | 2/2013 | Hu | | H04N 1/409 382/261 |
| 8,472,724 B2 * | 6/2013 | Lertrattanapanich | | G06T 5/002 382/205 |
| 8,514,302 B2 * | 8/2013 | Utsugi | | H04N 5/217 348/241 |
| 8,542,944 B2 * | 9/2013 | Sun | | G06K 9/40 382/128 |
| 9,265,475 B2 | 2/2016 | Yang et al. | | |
| 2008/0159643 A1 * | 7/2008 | Huang | | G06T 5/002 382/260 |
| 2009/0046943 A1 * | 2/2009 | Ishiga | | G06T 5/10 382/266 |
| 2012/0027319 A1 * | 2/2012 | Hu | | H04N 1/409 382/275 |
| 2014/0010472 A1 * | 1/2014 | Xu | | G06T 5/003 382/263 |
| 2014/0321768 A1 * | 10/2014 | Tsai | | G06T 5/002 382/263 |
| 2015/0010247 A1 * | 1/2015 | Tanaka | | H04N 1/409 382/254 |
| 2017/0256037 A1 * | 9/2017 | Li | | G06K 9/4661 |

\* cited by examiner

CBCT IMAGE PROCESSING METHOD

CROSS REFERENCE TO RELATED APPLICATIONS

The present application claims the benefit of U.S. Provisional application U.S. Ser. No. 62/398,585, provisionally filed on Sep. 23, 2016 entitled "CBCT IMAGE PROCESSING METHOD", in the name of Edward B. Gindele, incorporated herein in its entirety.

FIELD OF THE INVENTION

The invention relates generally to the field of imaging, and in particular to noise reduction in cone beam computed tomography (CBCT).

BACKGROUND

CBCT (Cone Beam Computed Tomography) systems are known. For example, U.S. Pat. No. 9,265,475 (Yang) METHOD AND APPARATUS FOR SCATTER CORRECTION FOR CBCT SYSTEM AND CONE-BEAM IMAGE RECONSTRUCTION (incorporated herein in its entirety by reference) wherein the CBCT system describes generation of a 3-D volume image using a set of 2-D (two-dimensional) projection images.

While such systems may have achieved certain degrees of success in their particular applications, there is a need for improvement.

Digital radiographic volume imaging provides three-dimensional (3-D) images that have been reconstructed from a series of 2-D images taken over a succession of angles of the x-ray source relative to the detector. Acquisition of the 2-D projection images used for cone beam CT employs a large-area digital detector, such as a digital radiography (DR) detector that is typically used for conventional single projection radiography.

Computed tomography (CT) systems, such as cone beam computed tomography (CBCT) or cone beam CT systems offer considerable promise as one type of diagnostic tool for providing 3-D volume images. Cone beam CT systems capture volume data sets by using a high frame rate flat panel digital radiography (DR) detector and an x-ray source, typically affixed to a gantry that revolves about the object to be imaged, directing, from various points along its orbit around the subject, a divergent cone beam of x-rays toward the subject. The CBCT system captures projection images throughout the source-detector orbit, for example, with one 2-D projection image at every degree increment of rotation. The projections are then reconstructed into a 3-D volume image using various techniques. Among the most common methods for reconstructing the 3-D volume image are filtered back projection (FBP) approaches. Alternate approaches include iterative processing methods that use a cyclic combination of successive reconstructions and forward projections, filtered upon each iteration in order to reduce error between the reconstruction and the original 2-D projections.

One factor that affects the quality of X-ray imaging overall and volume reconstruction in particular relates to noise inherent to projection image capture. Noise sources include continuously varying error caused by electrical noise or round-off error and discretely varying error resulting from x-ray photon fluctuation. A number of approaches have been proposed for compensating and correcting image noise. However, conventional image acquisition and reconstruction methods leave some room for improvement with respect to image noise. Thus, there would be advantages to volume imaging methods that can reduce noise without increasing dosage requirements.

SUMMARY OF THE INVENTION

It is an object of the present disclosure to advance the art of radiographic imaging, including diagnostic 3-D volume imaging. Embodiments disclosed herein offer methods that can help to reduce noise without introducing artifacts due to aggressive noise correction. Methods described herein can be used for forming reduced-noise images having any number of dimensions including, but not limited to, 2-D, 3-D, and 4-D images, for example.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a method for multi-dimensional image processing comprising: obtaining a multi-dimensional image having a plurality of data elements, each data element having a corresponding data value; forming a reduced noise image by repeated iterations of a process that estimates the data value for each of one or more data elements of interest p of the obtained image, after obtaining an initial estimate for the data element of interest p, by: (i) for each data element k in a group of data elements in the image, calculating a weighting factor for the data element k as a function of the difference between the estimated data value for the data element p and the corresponding data value of the data element k; (ii) updating the estimated data value for the data element p according to the combined calculated weighting factors and the data value of the data element k; and displaying, storing, or transmitting the reduced noise image.

From an alternate aspect, the present disclosure provides a method of noise filtering a multi-dimensional image that includes multiple data elements including the steps of: a) selecting a data element of interest; b) calculating a reduced noise value for the data element of interest using a combination of a first and second weighting factor, wherein the first weighting factor for each other data element is calculated by: i) selecting an estimate data value for the data element of interest; ii) evaluating a weighing function based on the difference between the other data element value and the estimate data value; iii) replacing the estimate data value with the reduced noise value and repeating steps i) and ii) one or more times; and wherein the second weighting factor for each other data element is calculated by: i) selecting a region about the data element of interest and a corresponding region about the other data element; ii) for each local data element in the region about the data element of interest, calculating a similarity metric based on the difference value between the local data element and its corresponding local data element in the region within the region about the other data element; iii) calculating the second weighing factor as the sum of similarity metric values; c) combining the first and second weighting factors to calculate the reduced noise value for the data element of interest; d) repeating steps b) and c) for other data elements in the multi-dimensional image to form the reduced noise multi-dimensional image;

and e) displaying, storing, or transmitting the reduced noise multi-dimensional image on a display.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1:
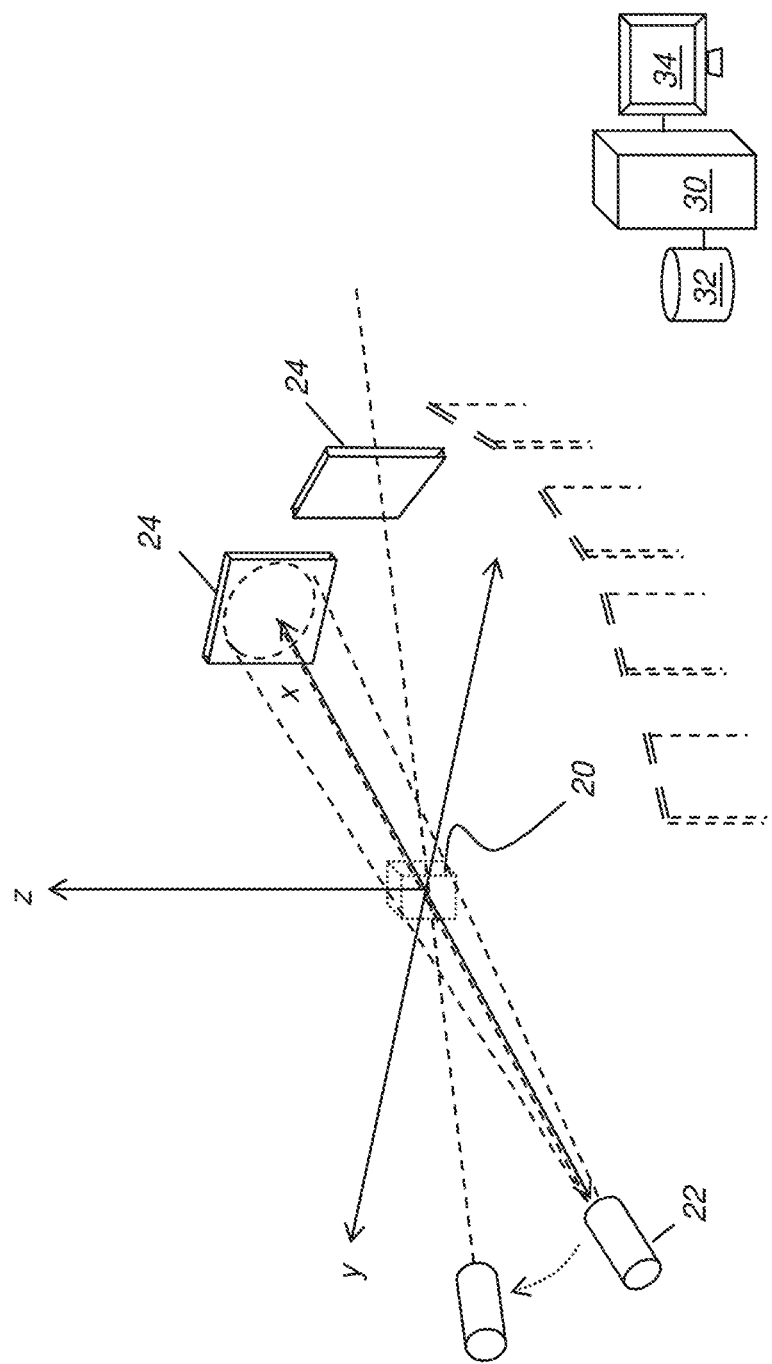
FIG. 1 is a block diagram schematic that shows how projection images are obtained.

The following is a detailed description of preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, the term "volume image" is synonymous with the terms "3-dimensional image" or "3-D image". Embodiments of the present invention are particularly well suited for suppressing the types of metal artifacts that occur in 3-D volume images, including cone-beam computed tomography (CBCT) as well as fan-beam CT images.

In the image processing context of the present disclosure, "rendering" is the active process of generating and forming an image for display and generating the pattern of signals needed for displaying it to a user. Image data content that is used for rendering can be transformed from a 2-D or 3-D model (or models), typically stored as scene content in some type of scene file, into suitable patterns of light energy that are emitted from a display screen. A scene file contains objects in a strictly defined language or data structure, describing aspects of the image content such as geometry, viewpoint, texture, lighting, and shading information as a description of a scene. The data contained in the scene content or scene file is passed to a rendering program to be processed and output or streamed to a display driver or graphics processing unit (GPU) for direct presentation on a display or to a digital image or raster graphics image file. The digital image data file can alternately be available for presentation on a display. In general, the term "rendering" provides a transformation that can be considered as analogous to an "artist's rendering" of a scene; different artists working in different media can generate different renderings of the same scene content. The same image content can be rendered, for example, on a monochrome display or in color on a full color display.

With respect to an image detector, the term "pixel" refers to a picture element unit cell containing a photo-conversion circuit and related circuitry for converting incident electromagnetic radiation to an electrical signal. For the image processing steps described herein, the terms "pixels" for picture image data elements, conventionally used with respect 2-D imaging and image display, and "voxels" for volume image data elements, often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, techniques described as operating upon pixels may alternately be described as operating upon the 3-D voxel data that is stored and represented in the form of 2-D pixel data for display. In the same way, techniques that operate upon voxel data can also be described as operating upon pixels.

It should further be noted that embodiments of the present disclosure can be applied to any type of multi-dimensional image that contains multiple data elements, including 2-D and 3-D images as well as images with additional dimensions, such as a 4-D image, wherein the first three dimensions relate to spatial position of a data element and the fourth dimension relates to time, for example. The embodiments described herein use the example of radiographic images, wherein the intensity data assigned to each data element relates to the relative density of the corresponding material to incident radiation. The data elements can be other types of data elements, including color data elements, for example. Data elements for 2-D images are typically termed pixels; for 3-D images, the data elements are termed voxels.

In the context of the present disclosure, the phrase "in signal communication" indicates that two or more devices and/or components are capable of communicating with each other via signals that travel over some type of signal path. Signal communication may be wired or wireless. The signals may be communication, power, data such as image data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members, but not containing every member of the full set. A "proper subset" of set S is strictly contained in set S and excludes at least one member of set S. A "partition of a set" is a grouping of the set's elements into non-empty subsets so that every element is included in one and only one of the subsets. Two sets are "disjoint" when they have no element in common.

CBCT imaging apparatus and the imaging algorithms used to obtain 3-D volume images using such systems are well known in the diagnostic imaging art and are, therefore, not described in detail in the present application. Some exemplary algorithms and approaches for forming 3-D volume images from the source 2-D images, projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat. No. 5,270,926 entitled "Method and Apparatus for Reconstructing a Three-Dimensional Computerized Tomography (CT) Image of an Object from Incomplete Cone Beam Data" to Tam.

Embodiments of the present invention can be readily adapted to the particular geometry of the CBCT or other volume imaging apparatus. In particular, an extremity imaging apparatus can generate volume images suitable for application of methods described herein.

In typical applications, a computer or other type of dedicated logic processor for obtaining, processing, and storing image data is part of the CT or CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present invention.

In order to more fully understand the methods of the present invention and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus for obtaining the individual 2-D images that are used to form a 3-D volume image. A cone-beam radiation source 22 directs a cone of radiation toward a subject 20, such as a patient or other subject. A sequence of images is obtained in rapid succession at varying angles about the subject, such as one image at each 1-degree angle increment in a 200-degree orbit. A DR detector 24 is moved to different imaging positions about subject 20 in concert with corresponding movement of radiation source 22. FIG. 1 shows a representative sampling of DR detector 24 positions to illustrate how these images are obtained relative to the position of subject 20. Once the needed 2-D projection images are captured in this sequence, a suitable imaging algorithm, such as filtered back projection (FBP) or other conventional technique, is used for generating the 3-D volume image. Image acquisition and program execution are performed by a computer 30 or by a networked group of computers 30 that are in image data communication with DR detectors 24. Image processing and storage is performed using a computer-accessible memory 32. The 3-D volume image can be presented on a display 34.

FBP is a discrete implementation of an analytic model that assumes that CT transmission measurements are linear functions of the attenuation line integrals along the corresponding primary photon trajectories through the subject and are noiseless. When scanning subjects comprised of only anatomically native materials under normal conditions, relatively simple corrections to the raw projection data are sufficient to assure that these assumptions (i.e. linear relationship) are at least approximately true. This treatment allows acquisition and processing of FBP images that are substantially free of visually observable artifacts. However, noise remains a well-known problem, as noted earlier.

The Applicants have developed a CBCT image processing method to generate a 3-D image that addresses the problem of image noise, wherein multiple filters can be applied during image processing, at different stages of the process. According to one embodiment, one filter is applied to the 2-D images and another filter is applied to the constructed 3-D volume image.

Analytical Processing Method

Figure 2:
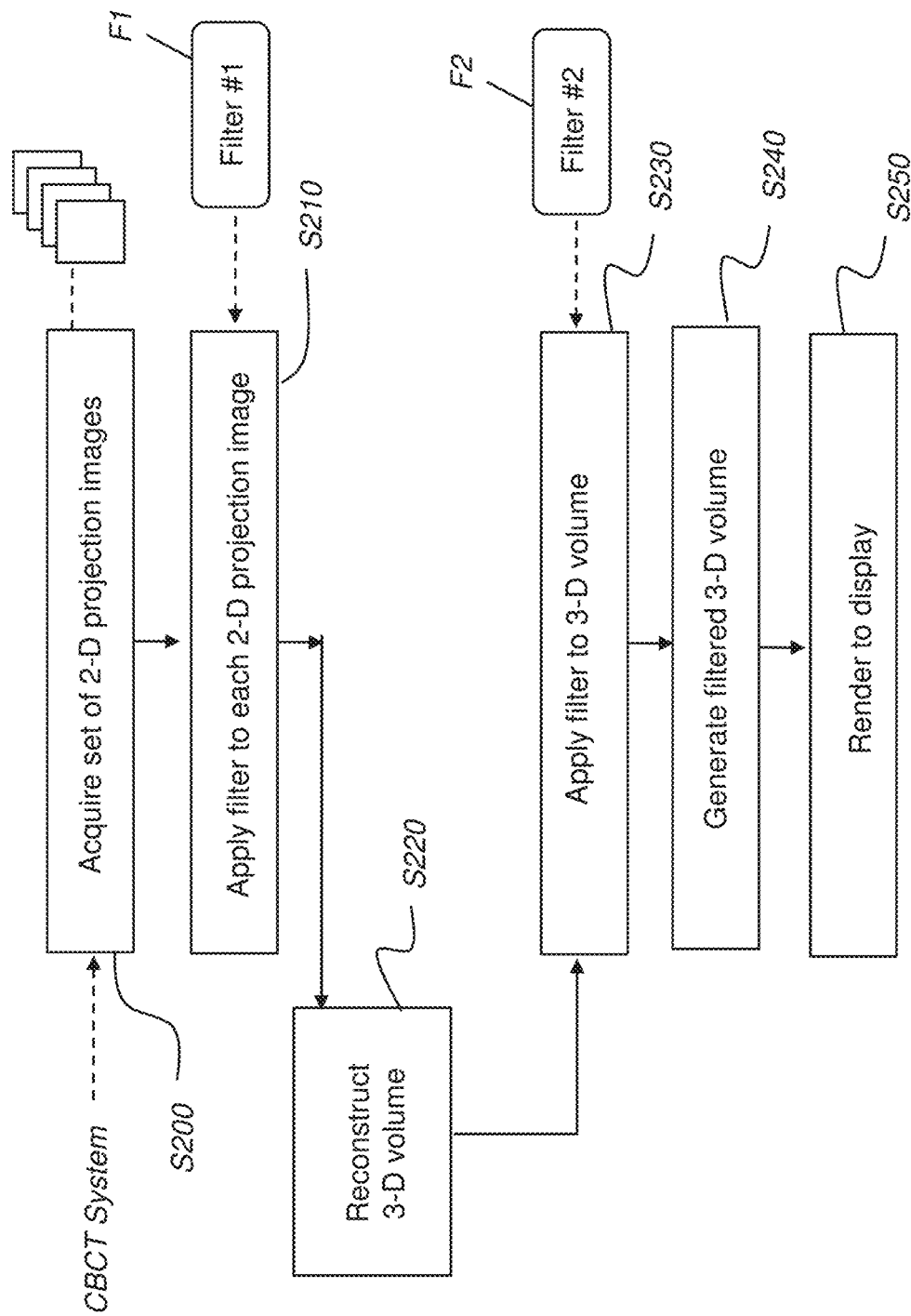
FIG. 2 is a logic flow diagram that shows a processing sequence for noise correction according to an embodiment of the present disclosure.

Referring to the logic flow diagram of FIG. 2, the method includes:

(1) using a CBCT system, acquiring a set of 2-D projection images in an acquisition step S200.

(2) in a filtering step S210 applying a First Filter F1 to each of the acquired 2-D projection images. This generates a set of filtered 2-D projection images.

(3) in a reconstruction step S220, generating a first 3-D volume image using the filtered 2-D projection images.

(4) in a filtering step S230, applying a Second Filter (F2) to the first 3-D volume image. Volume generation step S240 generates a second (filtered) 3-D volume image.

(5) in a display step S250, displaying, storing, or transmitting the second 3-D volume image.

Filter F1 can be the same or different than filter F2. Filters F1 and F2 can be, for example but not limited to, a sigma filter (such as an iterative Bayesian sigma filter as described herein, or a non-local sigma filter) or a bilateral filter. Note that a sigma filter may operate using a weighting aspect, but this is not a requirement.

In one arrangement, filter F1 is a noise reduction filter that calculates a weighted average of pixels in a local region about a pixel of interest wherein the weights for the pixels are calculated as the multiple of two probabilities: a first probability calculated using an iterative Bayesian Sigma filter and a second probability using a Non-Local Means filter. Filter F1 is applied to a set of 2-D images to produce a new set of noise-filtered images. The first probability can be calculated using an iterative form of the Bayesian Sigma filter wherein the intensity weighting function is adjusted based on the previous iteration filtering operation and the pixel values used to calculate the weight are unfiltered. In another arrangement, the filter F1 is applied to a set of 2-D projection radiography captured images, treated as a three dimensional time sequence of images wherein the filter F1 is applied as a 3-D noise filter.

In one arrangement, filter F2 is a 3-D noise filter applied to a 3-D volume image that calculates the filtered pixel values as described by the iterative Bayesian Sigma filter described above. In another arrangement, filter F2 is applied to the 2-D slices of a three dimensional volume image wherein the filter F2 is applied as a 2-D noise filter. In another embodiment, filter F2 is applied first, for example, to axial slices of a volume image and subsequently applied to the coronal or sagittal slices of the filtered volume image, wherein the filter F2 is applied as a 2-D noise filter.

Applicants' noise reduction filter "Non-Local Sigma" includes the combination of a Non-local Means filter with the Bayesian Sigma filter.

The "Bayesian Sigma" filter uses a pixel intensity weighting about an estimated pixel value associated with the value of the pixel-of-interest to calculate a noise-free pixel value. The filter is applied iteratively by using the filtered value from the last iteration to adjust the pixel intensity weighting function about the estimated pixel value. The first value of the estimated pixel value can be taken as the value of the pixel of interest. However, there are other useful methods for calculating the first estimated value such as, but not limited to, using a small local average of pixel values. The iteration cycle can be stopped at any point with the last noise-free pixel value used as the final noise-free pixel value. This algorithm can include a radial spatial weighting factor used in conjunction with the pixel intensity weighting. Note that a single-iteration Sigma filter used with a radial spatial weighting factor can be considered a "Bilateral" filter.

The "Non-local Means" algorithm uses local patches, or spatial regions located about a pixel-of-interest and calculates a similarity metric between the patch that contains the pixel-of-interest and other patches in the image that may not contain the pixel of interest. The similarity metric is then used as a weighting value for the central pixel of that patch. The noise-free pixel value is calculated as a weighted average of those pixels in the center of patches. There are no necessary constraints on the size of the patches used. Patch regions can overlap. The method of the present disclosure calculates the root-sum-squared difference, summed over the patch region, as the similarity metric.

In the context of the present disclosure, two regions of an image are said to be corresponding when they have the same shape and same number of data elements (pixels, voxels, etc.). Two data elements with the same relative positions in two different regions are considered to be corresponding data elements.

Iterative Bayesian Sigma Filter

Applicants now refer to Applicants' iterative "Bayesian" Sigma filter.

Typically, a Sigma filter operates by calculating a weighted average of local pixel values. The weight for a pixel is based on a Gaussian function of pixel intensity. Typically, the Gaussian function is centered, in the intensity domain, about the value of the pixel of interest. Iterative Sigma filters apply the filter repeatedly to the image values in each iteration. Specifically, the filter is applied once, and the second time the filter is applied, the input pixel values are the filtered values from the first iteration. This produces a progressively smoother image (not always desirable).

With Applicants' Bayesian Sigma filter, multiple iterations are performed. As many as ten iterations have been found to be useful. However, the results (filtered pixel values) of the last iteration are used to center the Gaussian function and the original noisy pixel values are used as input. This distinguishes this approach from iterative use of a more conventional "Sigma" filter. Applicants consider the results to be suitable improvement over using a single application of a "Sigma" filter or the successively iterative approach.

The Applicants' "Non-local Sigma" filter concept uses a modified form of the "Non-local Means" filter, familiar to those skilled in the image processing arts, with a denominator term as a function of the expected noise standard deviation value, to calculate a first probability P1. A typical "Non-local Means" filter does not include a term, or sensitivity to, the expected image noise magnitude. The added denominator term modification makes the Non-local Means filtration considerable more effective. That is, with this modification, image regions with varying noise levels are filtered for noise more effectively. The Applicants' "Bayesian Sigma" filter (also with a denominator term based on the expected noise magnitude) is used to calculate a second probability P2. The final weight for pixels located about the pixel of interest is formed by a combination of P1 and P2 as the multiple of probabilities P1 and P2. Experimentation with a range of image data has determined that the combined use of P1 and P2, i.e., the "Non-local Sigma" filter, produces noise-filtered images with less artifacts and less remaining noise.

Iterative Reconstruction Processing Method

An alternate approach to use of analytic 3-D reconstruction are iterative reconstruction techniques. Iterative processing uses a discretized representation of image space and identifies an unknown object function for the image content using iterative solutions of a system of linear equations. Each linear equation in this processing corresponds to one measured value as a linear combination of unknowns. A process of successive improvements more and more closely approximates the image content, based on comparing computed projection data with actual 2-D projection data acquired using the method described previously with respect to FIG. 1.

Iterative methods use various approaches to image reconstruction according to a number of components:

(i) an image model that is a discretization of the image domain into N distinct 2-D pixels or, correspondingly, 3-D voxels;

(ii) a system model relating the image to the acquired data;

(iii) a data model that describes the statistical relationship between measured data and the expected value of measurements, such as a Poisson or Gaussian model;

(iv) a governing principle that defines the desired image, typically expressed in terms of an objective function (I) or cost function; and (v) an algorithm for iteratively optimizing the objective or cost function.

Figure 3:
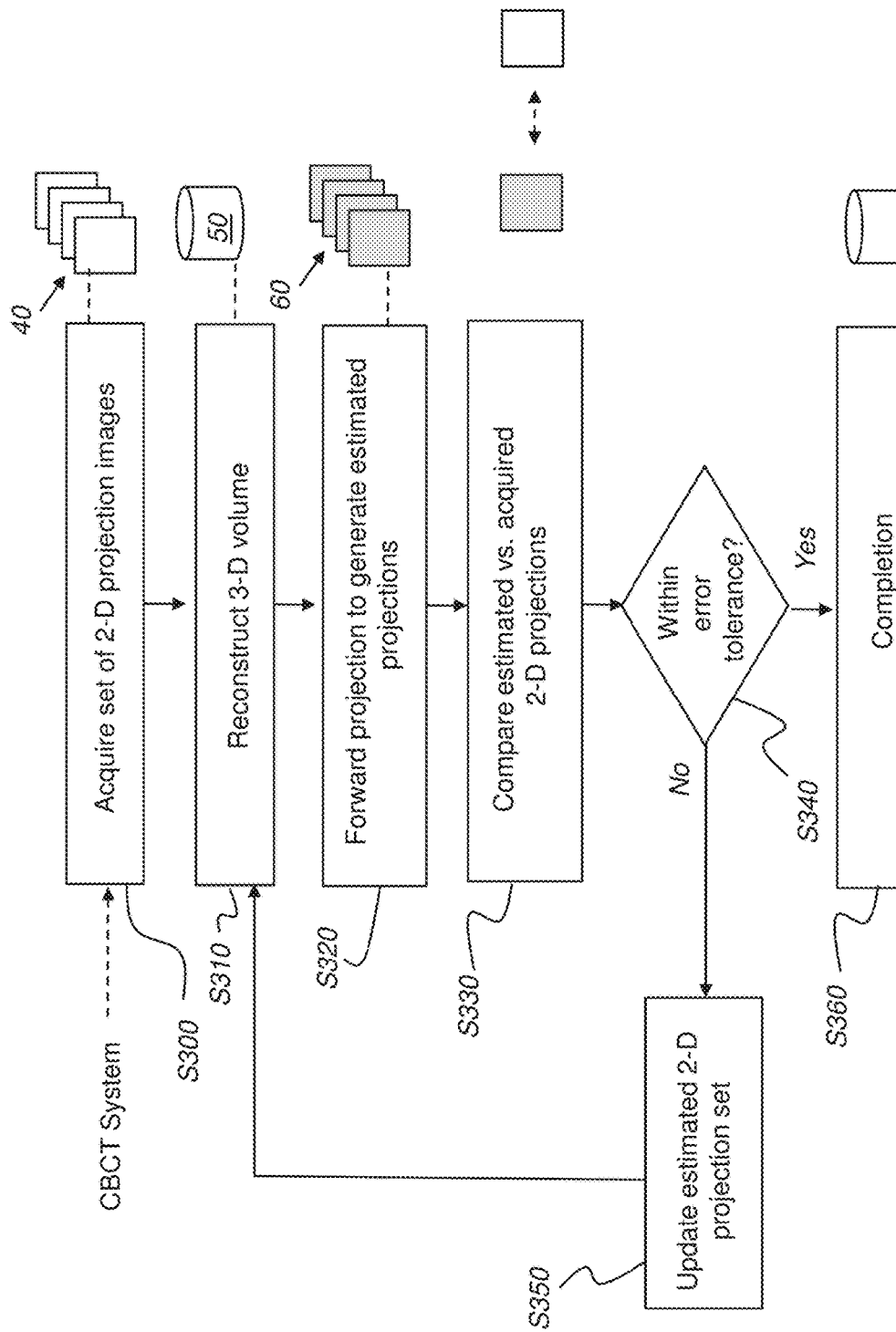
FIG. 3 is a logic flow diagram that shows iterative reconstruction processing steps.

FIG. 3 shows a simplified process flow for iterative reconstruction processing. A set of 2-D projection images 40 is captured in an acquisition step S300. An initial reconstruction step S310 forms a 3-D volume image 50, using an analytic reconstruction algorithm. In a forward projection step S320, processing logic generates a set of estimated projections 60, simulating 2-D projection acquisition using the reconstructed volume as its object. Forward projection simulates the x-ray projection at each of several projection angles through the reconstructed image volume of step S310, using a pattern of rays directed through the reconstructed object of volume image 50 to an image plane, forming a set of estimated or synthetic projection images 60, one estimated image corresponding to each projection angle.

Forward projection is widely applied in iterative reconstruction methods. One commonly used forward projection utility is referred to as a ray-tracer, in which each pixel is assumed to be formed by a ray extended between the position of the source and the pixel on the detector. As the ray travels through the reconstructed object space, the cumulative attenuation along the ray path is computed. The pixel data generated for this ray then forms the resulting pixel in the corresponding forward projection for that angle.

Continuing with the FIG. 3 sequence, a comparison step S330 compares computed values in each estimated projection image computed by the system with actual measured data from set of projection images 40. A results test step S340 calculates the difference between actual and computed values and determines whether or not further iterations are needed. If further iterations are indicated by the amount of difference, an update step S350 executes, updating the set of projection images that is used for volume reconstruction in step S310. If the amount of difference is within predetermined thresholds, a completion step S360 can execute, allowing the volume data to be stored, displayed, or transmitted.

Conventional iterative reconstruction algorithms typically work by first forming an objective function Φ that incorporates an accurate system model A, a statistical noise model, and a prior image model. The image f is reconstructed by computing an estimate $f^*$ that minimizes the objective function $\Phi(f)$:

$$\Phi(f) = R(f, \mu(r)) + H(f) \quad \text{(Eq. 1)}$$
$$f^* = \underset{f>0}{\operatorname{argmin}} \Phi(f)$$

wherein r represents the spatial coordinate (x,y,z); H(f) is the data fidelity term, and R(f) is the regularizer/prior image term. The parameter μ can be a scalar or spatially varying parameter that controls the relative effect of the regularizer data and prior term on the final reconstructed image content.

The data fidelity term H(f) encourages the reconstructed object f towards similarity to the original measured noisy projection p data. The "encouragement" constrains the computed reconstructed object f to the space defined by the regularizer term R(f). The data fidelity term H(f) incorporates a model for the measurement system composed of an accurate system model in a forward projection matrix A; a statistical noise model is incorporated into a statistical weighting matrix W. A common choice for the data fidelity term is in a quadratic form, as follows:

$$H(f) = \frac{1}{2}(Af - p)^T W(Af - p) = \frac{1}{2}\|Af - p\|_W^2 \quad \text{(Eq. 2)}$$

wherein A is an M×N matrix; $p=(p_1, p_1, \ldots p_M)$ is a vector of length M, and $f=(f_1, f_1, \ldots f_N)$ is a vector of length N.

The statistical weighting matrix W in Eq. 2 is inversely proportional to the covariances of the measured projection data p. The covariances are related to the captured photon statistics and related to preprocessing steps such as detector response and normalization, scatter and beam hardening correction, denoising of the measured projections, and the like. If the measurements are independent, the statistical weighting matrix W is a diagonal matrix with diagonal elements given by:

$$w_i = \frac{1}{\sigma^2(p_i)} \quad \text{(Eq. 3)}$$

wherein $\sigma^2(p_i)$ is the variance of ith projection measurement $p_i$. By way of example, the variance for a Poisson measurement process with independent electronic noise is given by:

$$\sigma^2(p_i) = \frac{I_i + \sigma_e^2}{I_i^2} = \frac{1}{I_{i0}}\exp(p_i)\left(1 + \frac{\sigma_e^2}{I_{i0}}\exp(p_i)\right) \quad \text{(Eq. 4)}$$

wherein $I_{i0}$ is the open field intensity; $I_i$ is the intensity of the ith projection measurement; and $p_i = -\log(I_i/I_{i0})$ is the density for the ith ray; and $\sigma_e^2$ is the variance of the sensing electronics.

The regularizer/prior term R(f) constrains (encourages or weights) the reconstructed image f according to prior knowledge about the image content to be reconstructed. Examples of prior knowledge models include smoothness and self similarity within the image, and similarity to a specific prior image or to a class of prior images. Regularizers enforce smoothness in the reconstructed images by constraining neighboring pixels to have similar values. These types of localized regularizers can be interpreted as a denoising operation, penalizing noise in the reconstructed image. Examples of this type of regularizer include total variation, Huber, Tikhonov, q-GGMRF, generalized total variation, higher order derivatives (e.g. Laplacian), etc.

Self-similarity regularizers operate on the principle that the reconstructed image will exhibit regions that are similar to one another. These types of regularizers such as non-local total variation are based upon the non-local means (patch-based) denoising approach. Prior image constrained compressed sensing (PICCS) enforces similarity between the reconstructed image and a prior image from a previous scan/reconstruction of the object.

Dictionary-based regularizers (e.g. K-SVD, as described in an article by Ahron, et al. entitled "K-SVD: An Algorithm for Designing Overcomplete Dictionaries for Sparse Representation" in *IEEE Transactions on Signal Processing*, Vol. 54 No. 11, November 2006) build a prior model of the image using a dictionary learned from a set of training (class of prior).

The dictionary-based regularizer is used to enforce similarity between the entries of the dictionary and the reconstructed image. In general, regularizers can be interpreted as providing a denoising operation and are analogous to denoising in image processing.

A number of different algorithms can be used for minimizing the objective function $f^*$. One strategy is to utilize so-called forward-backwards operator splitting (aka proximal gradient) methods to minimize the objective function. The operator-splitting technique simplifies and improves the computational efficiency of the minimization by splitting the regularizer term and data fidelity term into the following two step iterative algorithm:

(Eqs. 5)
$$v^{k+1} = f^k - \delta^k A^T W(Af^k - p) \quad \text{(i)}$$
$$f^{k+1} \leftarrow \underset{f>0}{\operatorname{minarg}}\left\{\mu R(f) + \frac{1}{2\delta^k}\|f - v^{k+1}\|^2\right\} \quad \text{(ii)}$$

wherein $A^T$ is the transpose of the forward projection matrix A; δ is a scalar parameter; and k is the iteration index. Value $v^{k+1}$ represents the reconstructed object at each step in the iteration. The updated image content at each iteration is $f^{k+1}$.

In the above operator-splitting sequence of eqs. 5, step (i) depends only on the choice of forward model A and performs a tomographic update that reinforces fidelity with the captured data from projections p. This is a gradient descent algorithm where the direction of the gradient, $A^T(Af^k-p)$, and a step size $\delta^k$ are used to update the current image $f^k$. Step (ii) depends only on the choice of regularizer and re-enforces the regularizer on the reconstructed object $v^{k+1}$ from step (i). The two steps iterate until a desired solution is obtained. The reconstructed image content can then be displayed, stored, or transmitted.

Regularization enforces smoothness in the reconstructed images by encouraging or constraining neighboring pixels to have similar values. These types of regularizers can be interpreted as a denoising operation and are analogous to denoising in image processing.

In step (i) of eqs. 5, a voxel independent constant step size $\delta^k$ is used in tomographic update. The global step size $\delta$, applied to each voxel, can be determined empirically, or from the Lipschitz's constant:

$$0 < \delta < \frac{2}{\|A^T W A\|} \quad \text{(Eq. 5.1)}$$

or by the following optimization:

$$\delta^k = \underset{\delta \geq 0}{\operatorname{argmin}}\{H(f^k - \delta A^T W(Af^k - p))\} \quad \text{(Eq. 6)}$$

wherein H( ) is the data fidelity term given by Eq. 2. The optimization problem can be solved approximately by using a 1-D line search method or in closed form given by:

$$\delta^k = \frac{(\nabla H(f^k))^T (\nabla H(f^k))}{(\nabla H(f^k))^T A^T W A (\nabla H(f^k))} \quad \text{(Eq. 7)}$$

Conventional iterative reconstruction techniques can often be computationally intensive and time-consuming, and can have results that show appreciable noise content. An embodiment of the present disclosure addresses the noise problem by providing filtering to various data structures that are used to generate the volume data. Referring to the logic flow diagram of FIG. 4, there is shown a sequence for iterative reconstruction. Noise filters NF are applied to set of acquired projection images 40 to provide filtered projection images 40'. Following the reconstruction step S310 in each iteration, noise filter NF is applied to the 3-D volume image 50 to provide a filtered volume image 50'. In addition, noise filter NF can also be applied to the estimated projections 60 that are calculated in forward projection step S320 in order to form filtered estimated projections 60'.

Figure 4:
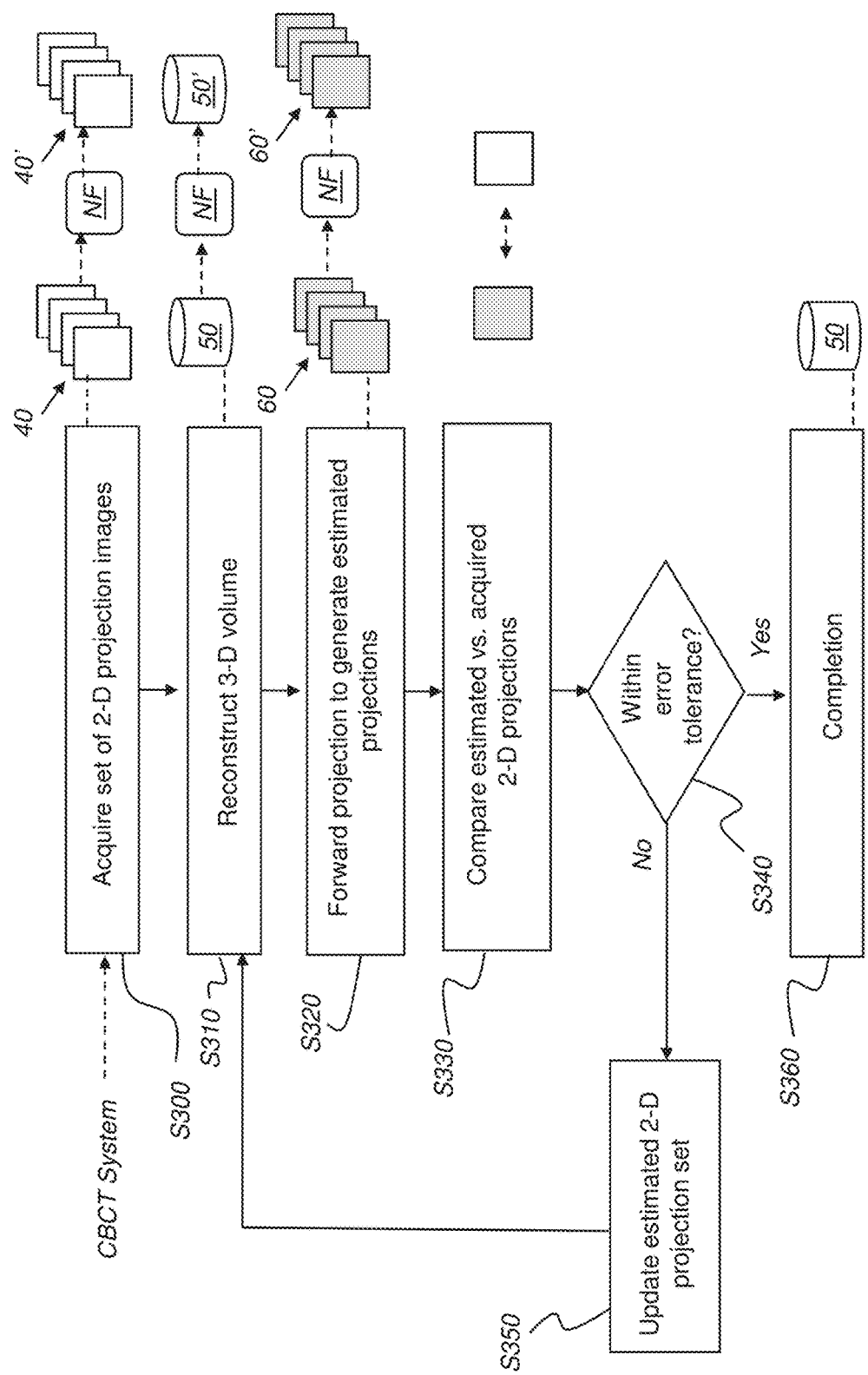
FIG. 4 is a logic flow diagram that shows the use of noise filtering in iterative reconstruction processing steps.

As noted previously, filter NF can be the same filter or type of filter for different stages of the FIG. 4 process, or can be different filter types.

Framework—Laplacian Pyramid

According to an embodiment of the present disclosure, noise filtering is applied at various stages of image processing that use a Laplacian pyramid infrastructure. Described in detail in U.S. Pat. No. 6,937,772 entitled "Multiresolution Based Method for Removing Noise from Digital Images" to Gindele, the Laplacian pyramid framework provides a structure for applying Non-local Sigma (NLS) noise filtering to image data. Although the technology described in the Gindele '772 disclosure is directed to 2-dimensional images, the present invention extends this algorithmic approach to 3-dimensional data sets. The Laplacian pyramid framework serves as a computationally efficient method to filter very low spatial frequency noise components.

The basic structure of a Laplacian pyramid framework is the same whether processing 2-D or 3-D image data sets. An original image is used as the initial image of the pyramid and is filtered with a smoothing filter, typically a Gaussian kernel. Next, the smoothed image is down-sampled to produce a lower resolution version of the initial image referred to as a base image. The base image, which is usually half the resolution of the initial image (in each linear dimension), is then interpolated back to the resolution of the initial image. This interpolated image is then subtracted from the initial image to form a residual image. In most cases, the residual image is stored in the memory of the initial image and the interpolated image is discarded. Thus, the residual image and the base image constitute a pyramid with two levels. The initial image can be reconstructed from this pyramid representation by interpolating the base image and adding the residual image. A reconstructed image formed using this method has the same resolution as the initial image and contains the exact same image pixel values.

The above procedure for creating a Laplacian pyramid representation of an initial image can be used recursively to create a pyramid representation with many levels. For example, the processing can be repeated using the base image as a second initial image. The process then forms a second residual image from the second base image, yielding a pyramid structure having three levels. The computational cost of producing more pyramid levels using this recursive processing is very small.

Within each recursive iteration, noise filtering can be applied to any of the constructed base images prior to the generation of the next pyramid level. This approach can be referred to as filtering during construction. Alternately, a pyramid can be constructed first, with the noise filtering performed when base images are reconstructed. The Applicant has found that either method works well at removing noise. Noise filtering can be applied prior to, during, and following reconstruction of the base image.

A useful aspect of applying noise filters in the context of forming a Laplacian pyramid is that the noise filter kernels (meaning the lateral extent of the filters) can be kept small, typically 3×3×3 or 5×5×5, while still affecting a large local region in the final reconstructed image.

Sigma Filter

While the above described Laplacian pyramid framework can be used with any noise filter, an embodiment of the present disclosure uses a Bayesian form of a Sigma filter to effectively remove noise from the initial and base images. In conventional application, a Sigma filter is a local filter, operating on pixels within a region that is local with respect to a pixel of interest. The Sigma filter applies non-linear averaging of pixel value logic to a pixel or voxel of interest.

The description that follows applies to 2-D pixels as well as to 3-D voxels or multi-dimensional data elements of more than 3 dimensions. For simplicity of description of the Sigma filter, references to pixels also apply to voxels and other n-dimensional elements, with appropriate dimensional expansion.

The noise-free pixel estimate ($p_o'$) for the pixel of interest is calculated by the following equations:

$$\alpha_k = e^{-(p_k - p_o)^2 / 2\varphi \sigma_n^2 - r^2 / 2\sigma_r^2} \quad \text{(Eq. 8)}$$

$$\Omega_k = \Sigma \alpha_k \quad \text{(Eq. 9)}$$

$$p_o' = (1/\Omega_k) \Sigma p_k \alpha_k / \Sigma \alpha_k \quad \text{(Eq. 10)}$$

wherein the quantity $\alpha_k$ represents a weighting factor for the $k^{th}$ pixel located about the pixel of interest. The value of $p_o$ is the original noise-corrupted pixel value. The quantity $\sigma_n$ represents the standard deviation of the expected noise corresponding to the pixel of interest. The quantity $\sigma_r$ represents a radial weighting factor and r represents the distance between the pixel of interest and the $k^{th}$ pixel. The quantity $\sigma_r$ is typically set through experimentation and according to assessment of processed images. The quantity $\varphi$, is an arbitrary noise filtering strength parameter typically set to 1.0.

Applicants' Sigma Filter

In general, Bayesian processes operate by continually updating data values as additional or improved data becomes available. The Applicants' "Bayesian" form of the Sigma filter applies the logic of the sigma filter recursively while, with each successive iteration, changing the value of $p_o$ in the above equation (8). In the above described Sigma filter logic, the value of $p_o$ is the original noise-corrupted pixel value, serving as a type of "prior" in Bayesian processing terminology. In the Bayesian processing logic sequence, with each iteration, the value of $p_o'$ from the previous iteration is substituted into the equation for original pixel value $p_o$. This updates the prior $p_o$ value with each iteration. Thus with each iteration of the equation, the center of the Gaussian weighting envelope for filtering is effectively re-positioned. The Applicants' Bayesian Sigma filter, using multiple iterations, generally produces superior image quality results when compared to processes using just one iteration of the Sigma filter logic. In particular, statistical outlier pixels are filtered more effectively than with a single iteration of the filtering logic. In practice, the Applicant has found that execution using about 5 to 7 iterations yields very good results.

Non-Local Means Filter

The non-local means filter is a noise filter, described in the literature, and used in the method of the present disclosure, to generate values used to formulate a new, hybrid filter. Non-local means filtering uses a weighting based on similarity of patches, throughout the image, to a given patch. Equations that describe the logic of the non-local means filter are as follows:

$$\omega_k = \Sigma_y e^{-(p_k(y)-p_o(y))^2/2\lambda\sigma_n^2} \qquad (Eq.\ 11)$$

$$\Gamma_k = \Sigma\omega_k \qquad (Eq.\ 12)$$

$$p_o' = (1/\Gamma_k)\Sigma p_k \omega_k \qquad (Eq.\ 13)$$

wherein a noise free pixel estimate $p_o'$ for the pixel of interest $p_o$ is calculated as a weighted average of local pixels.

The weighting factor $\omega_k$ is calculated for the $k^{th}$ pixel about the pixel of interest by taking a region about the pixel of interest and the corresponding region about the $k^{th}$ pixel. The two regions correspond by having the same shape and the same number of pixels or voxels. The calculated weighting factor $\omega_k$ is a measure of the similarity of the region about the $k^{th}$ pixel to the corresponding region about the pixel of interest. In similar fashion to the preceding description, the value $\lambda$ is an arbitrary noise filtering strength parameter, determined empirically.

Non-Local Bayesian Sigma Filter

It should be noted that the weighting factor $\omega_k$, given by the non-local means logic does not contain the same information as the weighting factor $\alpha_k$, given by the iterative, Bayesian Sigma logic, but provides complementary information that can be useful for noise filtering. Therefore, an embodiment of the present invention can combine these two different noise filtering logical approaches to form a single noise filter, i.e., the Non-local Sigma filter by applying the following equations:

$$\eta_k = \alpha_k \omega_k \qquad (Eq.\ 14)$$

$$\Theta_k = \Sigma\eta_k \qquad (Eq.\ 15)$$

$$p_o' = (1/\Theta_k)\Sigma p_k \eta_k \qquad (Eq.\ 16)$$

In essence, the weighting factor for each noise filter individually, i.e., the Bayesian Sigma filter and the Non-local means filter, can be considered a probability statement about the $k^{th}$ pixel. The method of the present disclosure uses a simple multiplicative equation (Eq. 14) to combine the probabilities from the two individual weighting factors $\alpha_k$ and $\omega_k$. However, those skilled in the art will recognize that the present invention can be used with other methods to combine these separate weighting factors as:

$$\eta_k = f(\alpha_k, \omega_k) \qquad (Eq.\ 17)$$

wherein $f(\ )$ is a generalized function of these two variables. For example, the combining function $f(\ )$ could be implemented as a neural-net solution using training image data examples to determine the internal coefficients.

It should be noted that while the Non-local Bayesian Sigma filter has been shown to be effective when used with Laplacian pyramid processing of the image or volume data, the same filter logic can be applied with other image processing approaches.

GUI to Adjust Filter Aggressiveness

Figure 5A:
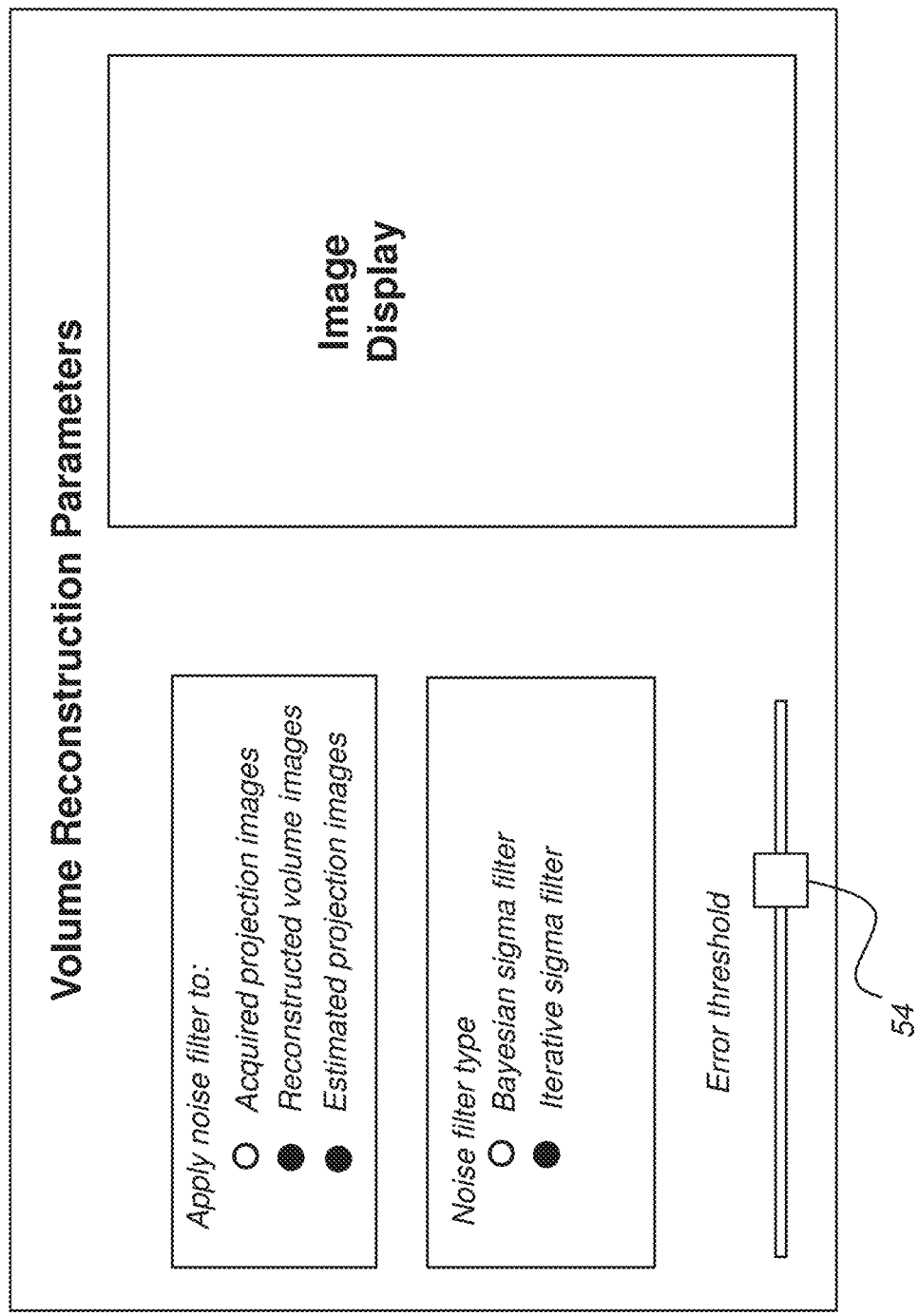
FIG. 5A is a schematic diagram that shows an operator interface for volume reconstruction parameters.

According to an embodiment of the present disclosure, an operator graphical user interface (GUI) can be provided to allow user adjustment of filter parameters. FIG. 5A shows an exemplary GUI 70 for noise filter specification and application. Selections can be made to apply noise filter NF to image content at one or more parts of the reconstruction process. Other selections allow the operator to specify a noise filter type and to adjust error threshold or overall filter aggressiveness, such as using a slidebar control 54, for example. A display area enables operator viewing of different 2-D and 3-D image content, including estimated projection images that are changing during the processing procedure.

Figure 5B:
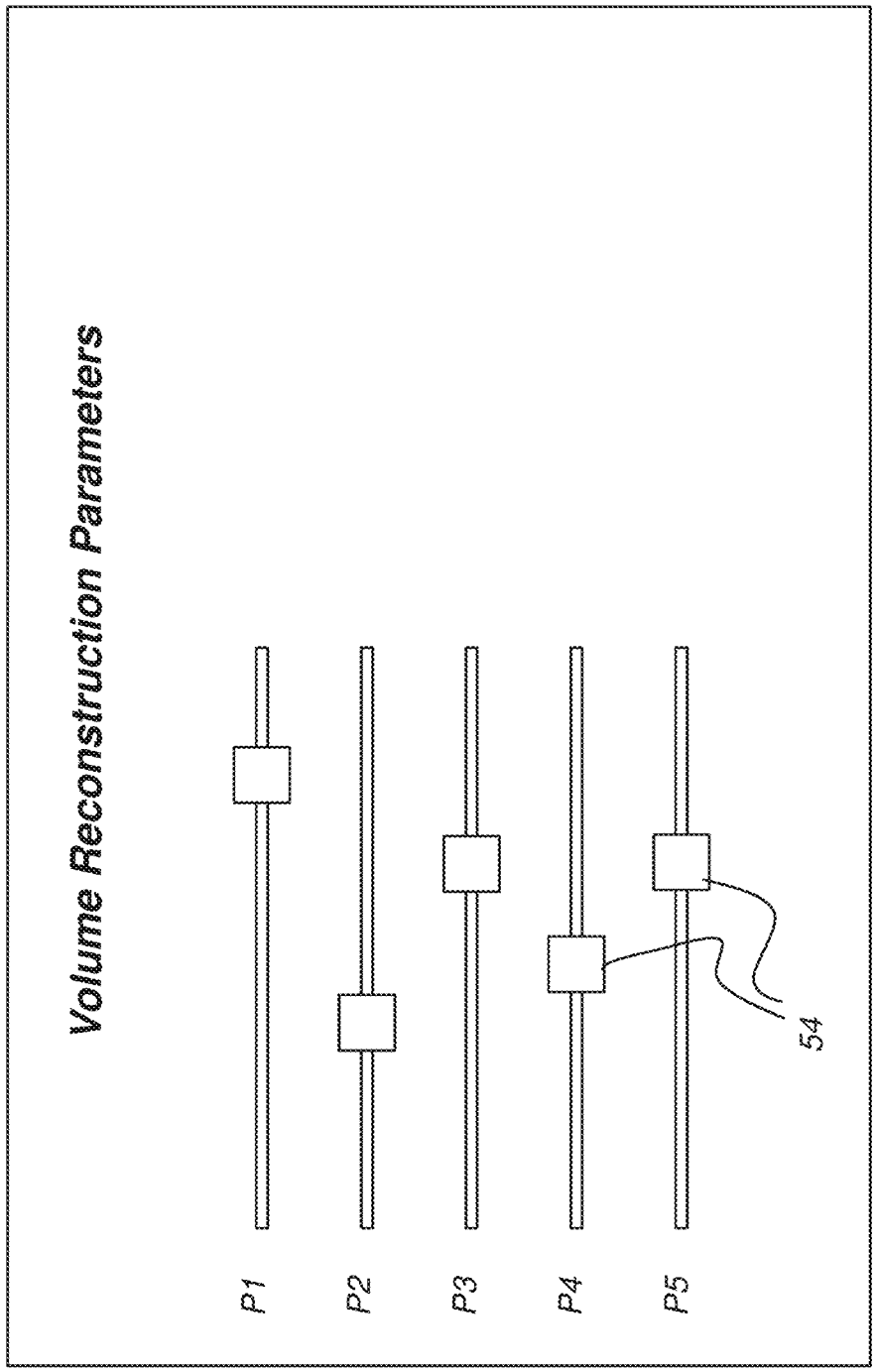
FIG. 5B is a schematic diagram showing an exemplary configuration screen for configuration adjustment of image processing.

The example of FIG. 5B shows a configuration screen for operator entry, showing values and settings that may be more suitable at installation or initial system configuration, rather than adjusted by the operator in standard use. Five parameter settings are shown by way of example only. One or more parameters P1, P2, P3, P4, and P5 can include various threshold, filtering, and variable weighting values, such as those described hereinabove with reference to equations 8 and 11, for example. Other parameters can affect processing by setting a number of iterations for the Bayesian Sigma filtering described hereinabove.

It can be appreciated that the GUI examples shown in FIGS. 5A and 5B are by way of example and can be adapted to either analytic or iterative processing.

In the description given herein, a preferred embodiment of the present invention will be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

In the following claims, the terms "first," "second," and "third," and the like, are used merely as labels, and are not intended to impose numerical requirements on their objects.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for multi-dimensional image processing comprising:
   obtaining a multi-dimensional image having a plurality of data elements, each data element having a corresponding data value;
   forming a reduced noise image by a plurality of process iterations estimating the data value for each of one or more data elements of interest p of the obtained image, after obtaining an initial estimate for the data element of interest p, by:
   (i) for each data element k in a group of data elements in the image, calculating a weighting factor for the data element k as a function of the difference between the estimated data value for the data element p and the corresponding data value of the data element k; and
   (ii) updating the estimated data value for the data element p according to the combined calculated weighting factors and the data value of the data element k; and
   displaying, storing, or transmitting the reduced noise image,
   wherein calculating the weighting factor for data element k further comprises calculating a similarity metric by:
   defining a first region of data elements that includes the data element of interest p;
   defining a corresponding region of data elements that includes the data element k; and
   generating the similarity metric according to comparison of data values of data elements in the first region about data element p with data values of corresponding data elements in the second region about data element k, and
   wherein the weighting factor is computed as a product of the generated similarity metric and a second value that is a function of the difference between the estimated data value for the multi-dimensional data element p and the corresponding data value of the multi-dimensional data element k.

2. The method of claim 1 wherein generating the similarity metric comprises applying a non-local means filter.

3. The method of claim 1 further comprising including the steps of forming the reduced noise image for portions of a Laplacian pyramid representation of the multi-dimensional image.

4. The method of claim 1 wherein the multi-dimensional image is a 2-D or 3-D radiographic image.

5. The method of claim 4 wherein the radiographic image is a cone-beam computed tomography image.

6. The method of claim 1 wherein the weighting factor is further calculated as a function of the separation distance between the data element k and the data element of interest p.

7. The method of claim 1 further comprising adjusting the weighting factor according to an operator instruction.

8. The method of claim 1 wherein the multi-dimensional image is a fluoroscopy image.

9. The method of claim 1 further comprising reducing the resolution of the multi-dimensional image.

10. The method of claim 1 applied to 2-D projection images prior to 3-D volume reconstruction.

11. The method of claim 10 further applied to the 3-D volume reconstruction.

12. The method of claim 1 further comprising transmitting or storing the reduced noise image data values.

13. A method for multi-dimensional image processing comprising:
   obtaining a multi-dimensional image having a plurality of data elements, each data element having a corresponding data value;
   forming a reduced noise image by a plurality of process iterations estimating the data value for each of one or more data elements of interest p of the obtained image, after obtaining an initial estimate for the data element of interest p, by:
   (i) for each data element k in a group of data elements in the image, calculating a weighting factor for the data element k as a function of the difference between the estimated data value for the data element p and the corresponding data value of the data element k; and
   (ii) updating the estimated data value for the data element p according to the combined calculated weighting factors and the data value of the data element k; and
   displaying, storing, or transmitting the reduced noise image,
   wherein the weighting factor is a first weighting factor and further comprising applying a second weighting factor to the data element of interest by:
   i) selecting a local region about the data element of interest and a corresponding region about another data element;
   ii) for each local data element in the local region about the data element of interest, calculating a similarity metric based on the difference value between the local data element and a corresponding data element within the corresponding region about the other data element; and iii) calculating the second weighing factor according to the sum of similarity metric values.

14. A method of noise filtering a multi-dimensional image that includes multiple data elements including the steps of:
   a) selecting a data element of interest;
   b) calculating a reduced noise value for the data element of interest using a combination of a first and second weighting factor;
   c) combining the first and second weighting factors to calculate the reduced noise value for the data element of interest;
   d) repeating steps b) and c) for other data elements in the multi-dimensional image to form the reduced noise multi-dimensional image; and
   e) storing, transmitting, or displaying the reduced noise multi-dimensional image on a display,
   wherein the second weighting factor for each other data element is calculated by:
   i) selecting a region about the data element of interest and a corresponding region about the other data element;
   ii) for each local data element in the region about the data element of interest, calculating a similarity metric based on the difference value between the local data element and its corresponding local data element in the region within the region about the other data element; and
   iii) calculating the second weighing factor as the sum of similarity metric values.

15. The method of claim 14 wherein the first weighting factor for each other data element is calculated by:
   i) selecting an estimate data value for the data element of interest;
   ii) evaluating a weighing function based on the difference between the other data element value and the estimate data value; and
   iii) replacing the estimate data value with the reduced noise value and repeating steps i) and ii) one or more times.

* * * * *

UNITED STATES PATENT AND TRADEMARK OFFICE
CERTIFICATE OF CORRECTION

PATENT NO. : 10,475,215 B2
APPLICATION NO. : 15/662670
DATED : November 12, 2019
INVENTOR(S) : Edward B. Gindele et al.

It is certified that error appears in the above-identified patent and that said Letters Patent is hereby corrected as shown below:

In the Specification

Column 8, Line 28-29    Please replace "typically expressed in terms of an objective function (1) or cost function; and" with -- typically expressed in terms of an objective function $\Phi$ or cost function; and --

Signed and Sealed this
Twenty-fourth Day of December, 2019

Andrei Iancu
*Director of the United States Patent and Trademark Office*